United States Patent

Nakada et al.

(10) Patent No.: US 8,772,739 B2
(45) Date of Patent: Jul. 8, 2014

(54) FLUORESCENCE DETECTION DEVICE AND FLUORESCENCE DETECTION METHOD

(75) Inventors: Shigeyuki Nakada, Tamano (JP); Kyouji Doi, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 566 days.

(21) Appl. No.: 13/148,556

(22) PCT Filed: Feb. 8, 2010

(86) PCT No.: PCT/JP2010/000740
§ 371 (c)(1), (2), (4) Date: Aug. 9, 2011

(87) PCT Pub. No.: WO2010/092785
PCT Pub. Date: Aug. 19, 2010

(65) Prior Publication Data
US 2012/0025098 A1 Feb. 2, 2012

(30) Foreign Application Priority Data
Feb. 13, 2009 (JP) ................................. 2009-032053

(51) Int. Cl.
*G01J 1/58* (2006.01)
*G01N 21/64* (2006.01)

(52) U.S. Cl.
USPC ............... 250/459.1; 250/458.1; 250/461.2

(58) Field of Classification Search
CPC .......... G01N 21/6408; G01N 21/6428; G01N 15/1459; G01N 2201/0691
USPC ................... 250/459.1, 458.1, 461.2
See application file for complete search history.

(56) References Cited

U.S. PATENT DOCUMENTS 4,716,363 A 12/1987 Dukes et al.
(Continued)

FOREIGN PATENT DOCUMENTS

| EP | 1 063 501 A1 | 12/2000 |
| JP | 2645270 B2 | 5/1997 |
| JP | 10 10049 A | 1/1998 |
| JP | 2000-501838 A | 2/2000 |

(Continued)

OTHER PUBLICATIONS

Extended European Search Report of the corresponding European Application No. 10 74 1065.6, dated Sep. 28, 2012.

*Primary Examiner* — David Porta
*Assistant Examiner* — Kenneth J Malkowski
(74) *Attorney, Agent, or Firm* — Global IP Counselors, LLP

(57) ABSTRACT

A fluorescence detection device generates a modulation signal for modulating the intensity of the laser light and modulates the laser light using the modulation signal. The detection device obtains a fluorescent signal of the fluorescence emitted by the measurement object irradiated with the laser light, and calculates, from the fluorescent signal, a fluorescence intensity and the phase delay of the fluorescence with respect to the modulation signal. At the time, the detection device controls the operation amounts of the signal level of a DC component of the modulation signal and the gain of amplification just after the output of the fluorescent signal so that the value of a fluorescence intensity signal falls within a preset range. After the operation amounts are settled, the detection device calculates the fluorescence intensity and then calculates the fluorescence relaxation time of the fluorescence emitted by the measurement object using the phase delay.

10 Claims, 6 Drawing Sheets

(56) References Cited

U.S. PATENT DOCUMENTS

| | | |
|---|---|---|
| 5,317,162 A | 5/1994 | Pinsky et al. |
| 5,879,900 A | 3/1999 | Kim et al. |
| 2003/0099574 A1 | 5/2003 | Bentsen et al. |
| 2009/0012721 A1 | 1/2009 | Kimura et al. |
| 2009/0218515 A1* | 9/2009 | Tjin et al. .................. 250/459.1 |
| 2009/0283699 A1 | 11/2009 | Baltz et al. |

FOREIGN PATENT DOCUMENTS

| | | |
|---|---|---|
| JP | 2001-59811 A | 3/2001 |
| JP | 2002-228586 A | 8/2002 |
| JP | 2005-501256 A | 1/2005 |
| JP | 2006-226698 A | 8/2006 |
| JP | 2007-512504 A | 5/2007 |
| JP | 2007-240424 A | 9/2007 |

* cited by examiner

FLUORESCENCE DETECTION DEVICE AND FLUORESCENCE DETECTION METHOD

TECHNICAL FIELD

The present invention relates to a device and a method for detecting fluorescence by processing a fluorescent signal obtained by receiving fluorescence emitted by a measurement object irradiated with laser light.

BACKGROUND ART

A flow cytometer for use in medical and biological fields includes a fluorescence detection device that receives fluorescence emitted by a fluorochrome in a measurement object irradiated with laser light and identifies the kind of the measurement object.

More specifically, in the flow cytometer, a suspension liquid containing a measurement object such as a biological material (e.g., cells, DNA, RNA, enzymes, or proteins) labeled with a fluorescent reagent is allowed to flow through a tube together with a sheath liquid flowing under pressure at a speed of about 10 m/sec or less to form a laminar sheath flow. The flow cytometer receives fluorescence emitted by a fluorochrome attached to the measurement object by irradiating the measurement object in the laminar sheath flow with laser light and identifies the measurement object by using the fluorescence as a label.

The flow cytometer can measure, for example, the relative amounts of DNA, RNA, enzymes, proteins, etc. contained in a cell and can quickly analyze their properties. Further, a cell sorter or the like is used to identify a specific type of cell or chromosome based on fluorescence and selectively and quickly collect only the identified cells or chromosomes alive.

The use of such a cell sorter is required to quickly and accurately identify more kinds of measurement objects from information about fluorescence.

Patent Document 1 discloses a fluorescence detection device and a fluorescence detection method which are capable of accurately and quickly identifying many kinds of measurement objects by calculating the fluorescence lifetime (fluorescence relaxation time) of fluorescence emitted by a measurement object irradiated with laser light.

Patent Document 1 describes that the fluorescence relaxation time is calculated from the phase delay of a fluorescent signal of fluorescence emitted by a measurement object irradiated with intensity-modulated laser light with respect to a modulation signal used for modulating the intensity of laser light.

PRIOR ART DOCUMENT

Patent Document

Patent Document 1: Japanese Patent Application Laid-Open No. 2006-226698

SUMMARY OF INVENTION

Technical Problem

The device and method disclosed in Patent Document 1 are capable of accurately and quickly calculating a fluorescence intensity and a fluorescence relaxation time, but the range of a fluorescence intensity that can be calculated with a given accuracy and the range of a fluorescence relaxation time that can be calculated with a given accuracy are limited. This results from that the contribution of a phase delay to a fluorescence relaxation time is not constant but is nonlinearly changed. Further, there is also a case where the fluorescence intensity and the phase delay have a large error caused by a quantization error during AD conversion due to contamination by noise components generated by constituent circuits. For this reason, the device and method disclosed in Patent Document 1 have a problem that a fluorescence intensity and a fluorescence relaxation time cannot be calculated with a given accuracy.

In order to solve the above problem, it is an object of the present invention to provide a fluorescence detection device and a fluorescence detection method which can calculate a fluorescence intensity and a fluorescence relaxation time with a given accuracy over wide ranges.

Solution to Problem

According to an aspect of the invention, there is provided a fluorescence detection device by processing a fluorescent signal obtained by receiving fluorescence emitted by a measurement object which is irradiated with laser light.

The device includes:

a light source unit operable to emit laser light with which a measurement object is irradiated while modulating an intensity of the laser light;

a light-receiving unit operable to output a fluorescent signal of fluorescence emitted by the measurement object irradiated with the laser light;

a light source control unit operable to generate a modulating signal for modulating the intensity of the laser light emitted from the light source unit;

a first processing unit that includes an amplifier that amplifies the fluorescent signal outputted by the light-receiving unit, a mixer that generates a component of the amplified fluorescent signal in phase with the modulation signal and a 90 degrees phase-shifted component of the amplified fluorescent signal which is phase-shifted by 90 degrees with respect to the modulation signal, and an AD converter that digitizes the generated in-phase component and 90 degrees phase-shifted component;

a second processing unit operable to calculate, by using the digitized in-phase component and the 90 degrees phase-shifted component, a fluorescence intensity signal and a phase delay of the fluorescence with respect to the modulation signal and operable to calculate, by using the calculated fluorescence intensity signal and the phase delay, a fluorescence intensity and a fluorescence relaxation time of the fluorescence emitted by the measurement object; and a signal control unit operable to control an operation amount of at least one of a signal level of a DC component of the modulation signal used for intensity modulation and a gain of the amplifier so that a value of the fluorescence intensity signal falls within a preset range.

According to another aspect of the invention, there is provided a fluorescence detection method by processing a fluorescent signal obtained by receiving fluorescence emitted by a measurement object which is irradiated with laser light.

The method includes the steps of:

generating a modulation signal by setting a frequency for modulating an intensity of laser light emitted from a laser light source unit and a signal level of a DC component to modulate laser light by using the modulation signal;

obtaining a fluorescent signal of fluorescence emitted by a measurement object irradiated with the laser light;

amplifying the fluorescent signal, generating a in phase-component of the amplified fluorescent signal with the modulation signal and a 90 degrees phase-shifted component of the amplified fluorescent signal which is phase-shifted by 90 degrees with respect to the modulation signal, and digitizing the generated in-phase component and the 90 degrees phase-shifted component;

calculating, by using the digitized in-phase component and the 90 degrees phase-shifted component, a fluorescence intensity and a phase delay of the fluorescence with respect to the modulation signal;

controlling an operation amount of at least one of the signal level of the DC component and a gain of the amplification so that the fluorescence intensity falls within a preset range; and calculating, by using the in-phase component and the 90 degrees phase-shifted component obtained under a condition of the operation amount at a time when a value of the fluorescence intensity falls within the preset range, a value of the fluorescence intensity signal and the phase delay and calculating, by using the calculated value of the fluorescence intensity signal and the calculated phase delay, a fluorescence intensity and a fluorescence relaxation time of the fluorescence emitted by the measurement object.

Advantageous Effects of Invention

According to the present invention, it is possible to provide a fluorescence detection device and a fluorescence detection method which can calculate a fluorescence intensity and a fluorescence relaxation time with a given accuracy over wide ranges.

DESCRIPTION OF EMBODIMENTS

Hereinbelow, the present invention will be described in detail based on a flow cytometer appropriately using a fluorescence detection device according to the present invention.

Figure 1:
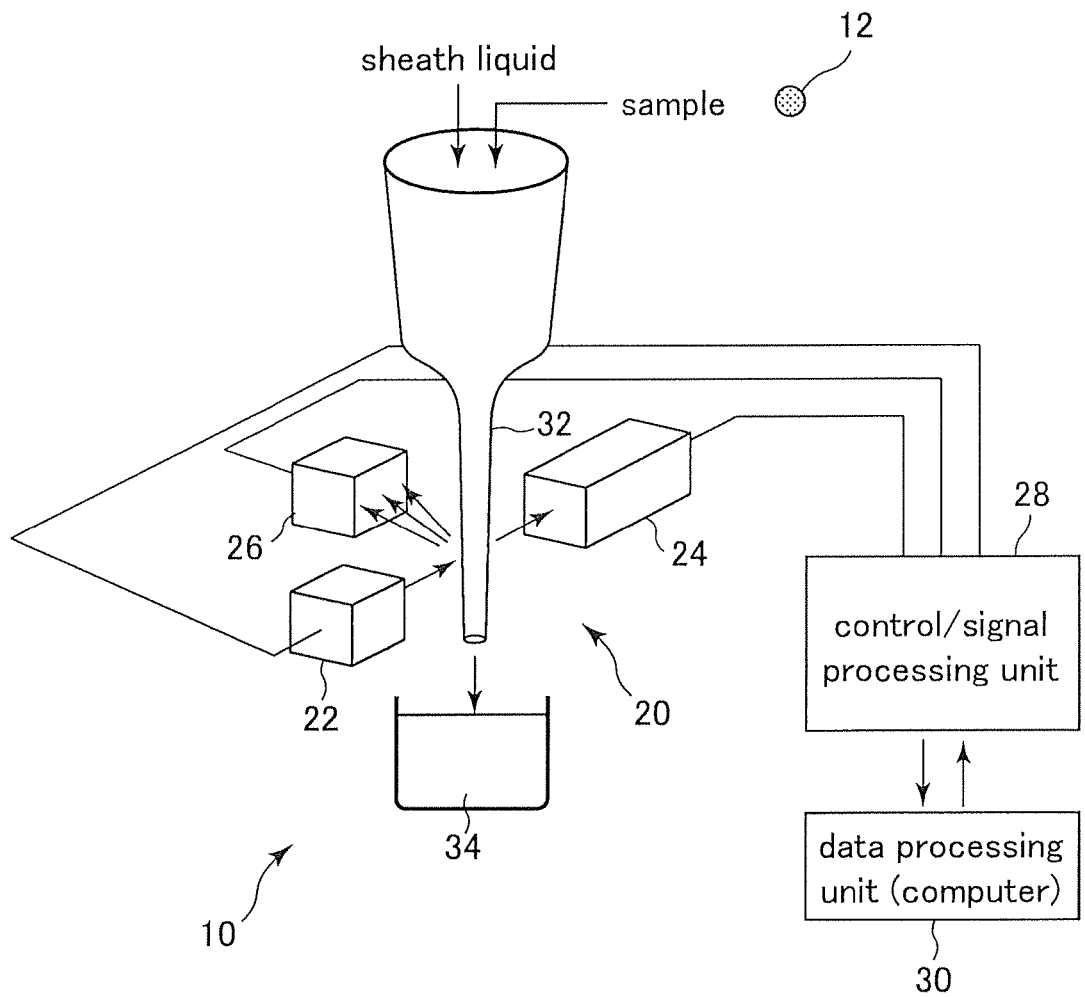
FIG. 1 is a schematic diagram illustrating the structure of a flow cytometer using a fluorescence detection device according to the present invention.

FIG. 1 is a schematic diagram illustrates the structure of a flow cytometer 10 using the fluorescence detection device according to the present invention.

Figure 2:
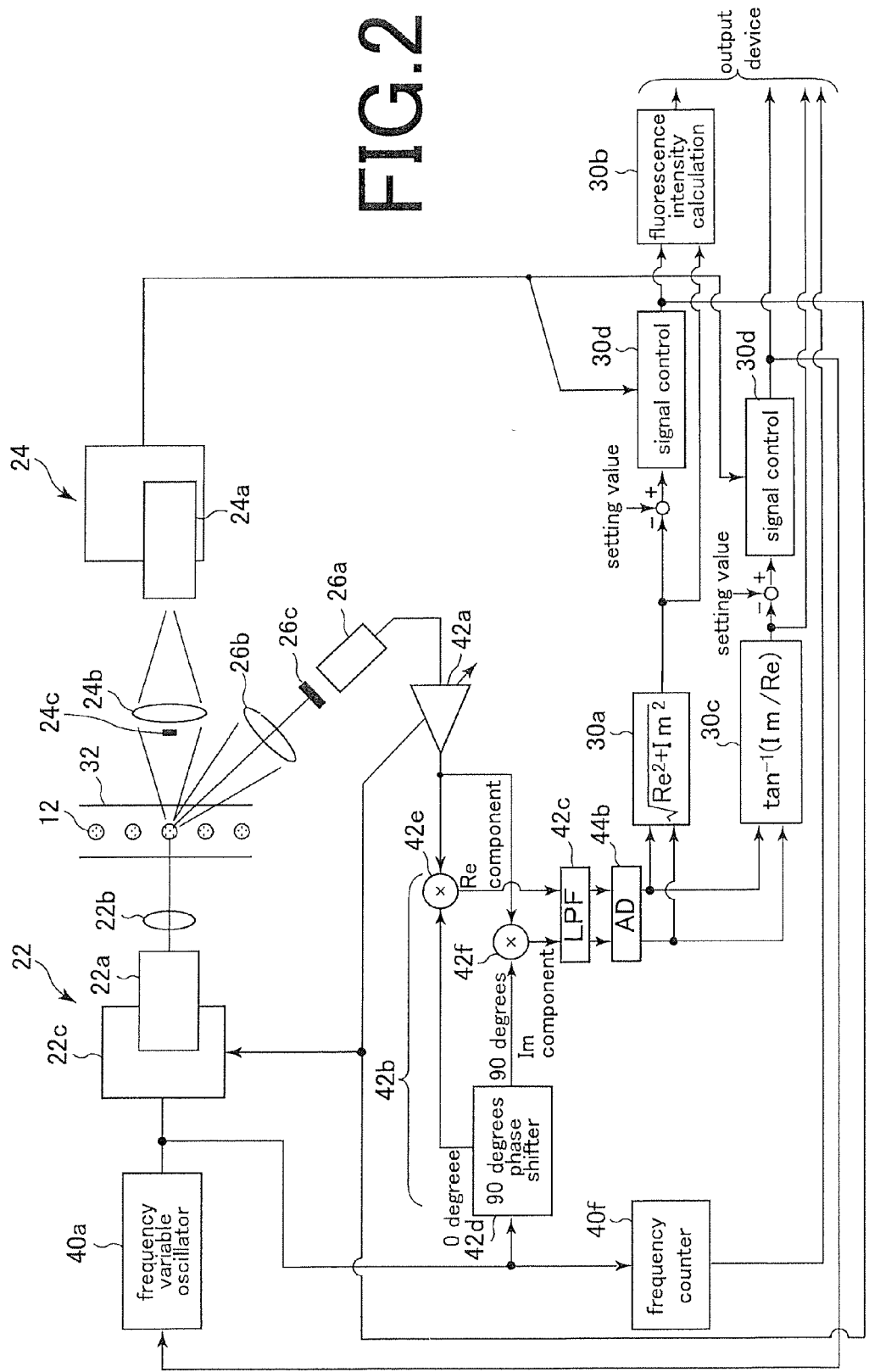
FIG. 2 is a diagram mainly illustrating the flow of signals in the flow cytometer illustrated in FIG. 1.

FIG. 2 is a diagram mainly illustrating the flow of signals in the flow cytometer 10.

The flow cytometer 10 mainly includes a laser light source unit 22, light-receiving units 24 and 26, a control/signal processing unit 28, a data processing unit (computer) 30, a tube 32, and a collection vessel 34.

The laser light source unit 22 emits laser light having a wavelength within a visible light band of 350 to 800 nm while modulating the intensity of the laser light by a controlled modulation signal. The modulation frequency and signal level of a DC component of the modulation signal are controlled.

The laser light source unit 22 includes a laser light source 22a, a lens system 22b (see FIG. 2), and a laser driver 22c (see FIG. 2). The laser light source 22a emits laser light of a predetermined wavelength as CW (continuous-wave) laser light of constant intensity while frequency-modulating the intensity of the CW laser light. The lens system 22b (see FIG. 2) focuses laser light on a predetermined measurement point (measurement field) in the tube 32. The laser driver 22c (see FIG. 2) drives the laser light source 22a.

As described above, the laser light source unit 22 includes one laser light source, but the number of laser light sources employed is not limited to one. The laser light source unit 22 may employ two or more laser light sources. In this case, it is preferred that laser beams emitted from two or more laser light sources of the laser light source unit 22 are combined together by, for example, a dichroic mirror to emit a laser beam to the measurement field.

As the light source that emits laser light, for example, a semiconductor laser is used. The laser light has an output of, for example, about 5 to 100 mW. On the other hand, the frequency (modulation frequency) at which the intensity of the laser light is modulated has a periodical cycle time slightly longer than a fluorescence relaxation time, and is, for example, 10 to 200 MHz.

The laser driver 22c provided in the light source unit 22 is configured so as to control the level of the DC component of intensity of laser light and the frequency for intensity modulation. That is, the intensity of laser light shows a change caused by superimposing intensity modulation at a given frequency on the DC component, and the minimum intensity of laser light is larger than 0.

The light-receiving unit 24 includes a photoelectric converter 24a (see FIG. 2), a lens system 24b (see FIG. 2), and a shielding plate 24c (see FIG. 2). The lens system 24b focuses forward-scattered light on the photoelectric converter 24a.

The photoelectric converter 24a is arranged so as to be opposed to the laser light source unit 22 with the tube 32 being provided therebetween. The photoelectric converter 24a receives laser light forward-scattered by the sample 12 passing through the measurement field, and outputs a detection signal indicating the passage of the sample 12 through the measurement field.

The shielding plate 24c is provided in front of the lens system 24b so as to face the sample 12 to prevent laser light from directly entering the photoelectric converter 24a. The signal outputted from the light-receiving unit 24 is supplied to the control/signal processing unit 28 and the data processing unit 30, and is used in the control/signal processing unit 28 and the data processing unit 30 as a trigger signal to inform the timing of the passage of the sample 12 through the measurement field in the tube 32 and as an OFF signal for terminating measurement.

On the other hand, the light-receiving unit 26 is arranged in a direction perpendicular to a direction in which laser light emitted from the laser light source unit 22 travels and to a direction in which the sample 12 moves in the tube 32. The light-receiving unit 26 includes a photoelectric converter 26a (see FIG. 2) that receives fluorescence emitted by the sample 12 irradiated with laser light in the measurement field.

The light-receiving unit 26 further includes, in addition to the photoelectric converter 26a, a lens system 26b (see FIG. 2) and a band-pass filter 26c (see FIG. 2). The lens system 26b focuses a fluorescent signal from the sample 12.

The lens system 26b is configured so as to focus fluorescence received by the light-receiving unit 26 on the light-receiving surface of the photoelectric converter 26a. The band-pass filter 26c has a transmission wavelength band set to perform filtering to allow the photoelectric converter 26a to receive fluorescence of a predetermined wavelength band.

As described above, the light-receiving unit 26 includes one photoelectric converter 26a, but may include two or more photoelectric converters. In this case, the light-receiving unit 26 may have a structure in which a dichroic mirror is provided in front of the band-pass filter 26c to separate fluorescence according to a frequency band and separated beams of the fluorescence are received by two or more photoelectric converters, respectively.

The band-pass filter 26c is provided in front of the light-receiving surface of each of the photoelectric converters 26a, and transmits only fluorescence of a predetermined wavelength band. The wavelength band of fluorescence that can pass through the band-pass filter is set so as to correspond to the wavelength band of fluorescence emitted by a fluorochrome.

The photoelectric converter 26a is equipped with, for example, a photomultiplier as a sensor to serve as a sensor that converts light received on its photoelectric surface into an electrical signal. Here, fluorescence received by the photoelectric converter 26a is intensity-modulated fluorescence because the fluorescence is emitted by irradiation with intensity-modulated laser light, and therefore a fluorescent signal outputted by the photoelectric converter 26a is a signal having the same frequency as the intensity-modulated laser light. The florescent signal is supplied to the control/signal processing unit 28.

Figure 3:
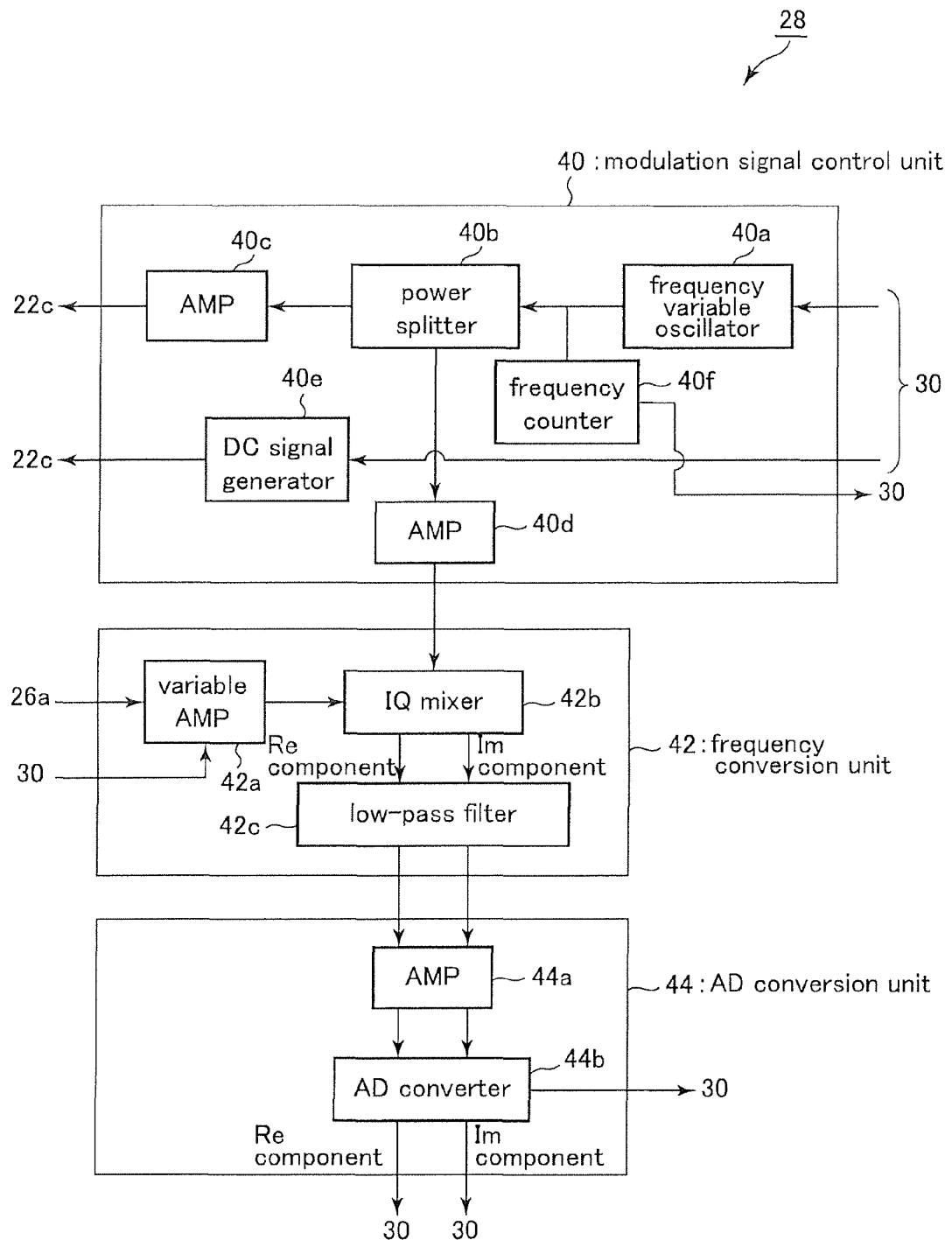
FIG. 3 is a schematic diagram illustrating the structure of a control/signal processing unit of the flow cytometer illustrated in FIG. 1.

FIG. 3 is a diagram illustrating the structure of the control/signal processing unit 28. The control/signal processing unit 28 includes a modulation signal control unit 40, a frequency conversion unit 42, and an AD conversion unit 44.

The modulation signal control unit 40 generates a modulation signal for modulating the intensity of laser light, and supplies the generated modulation signal to the laser driver 22c and the frequency conversion unit 42.

The modulation signal control unit 40 includes a frequency variable oscillator 40a, a power splitter 40b, amplifiers 40c and 40d, a DC signal generator 40e, and a frequency counter 40f.

The frequency variable oscillator 40a oscillates at a given frequency according to a control signal supplied from the data processing unit 30 to generate a modulation signal. As the frequency variable oscillator 40a, for example, a voltage-controlled oscillator is preferably employed.

The power splitter 40b evenly splits the generated modulation signal, and supplies the split modulation signals to the amplifiers 40a and 40d, respectively.

The amplifier 40c amplifies the modulation signal and supplies the amplified modulation signal to the laser driver 22c. The amplifier 40d amplifies the modulation signal, and supplies the amplified modulation signal to the frequency conversion unit 42 which will be described later. The modulation signal supplied to the frequency conversion unit 42 is used as a reference signal to determine the phase delay of the fluorescent signal outputted from the light-receiving unit 26 with respect to the modulation signal.

The DC signal generator 40e generates the DC component of the modulation signal and supplies the generated DC component to the laser driver 22c. The reason why the signal of the DC component is supplied to the laser driver 22c is to adjust the intensity of laser light so that the intensity of fluorescence emitted by the sample 12 is adjusted to a predetermined level to ensure highly-accurate calculation of the value of a phase delay and highly-accurate calculation of a fluorescence relaxation time using the phase delay. That is, the signal of the DC component is supplied to the laser driver 22c so that the intensity of laser light makes a change caused by superimposing intensity modulation on the DC component and the minimum intensity of laser light becomes larger than 0.

The frequency counter 40f counts the frequency of the modulation signal generated by the frequency variable oscillator 40a. The result of counting the frequency of the modulation signal by the frequency counter 40f is supplied to the data processing unit 30.

The frequency variable oscillator 40a and the DC signal generator 40e are both connected to the data processing unit 30, and the frequency of the modulation signal and the signal level of the DC component are controlled by control signals supplied from the data processing unit 30.

The frequency conversion unit 42 performs frequency-down conversion on the fluorescent signal supplied from the light-receiving unit 26a. The frequency conversion unit 42 mainly includes a variable oscillator 42a, an IQ mixer 42b, and a low-pass filter 42c.

The variable oscillator 42a amplifies the fluorescent signal. The variable amplifier 42a is connected to the data processing unit 30 to control its gain according to a control signal supplied from the data processing unit 30.

The IQ mixer 42b performs frequency-down conversion on the amplified fluorescent signal by using the modulation signal supplied from the modulation signal control unit 40 as a reference signal to generate the fluorescent signal in phase with the modulation signal and the fluorescent signal whose phase is shifted by 90 degrees with respect to the modulation signal.

The IQ mixer 42b includes a 90 degrees phase shifter 42d (see FIG. 2), a mixer 42e (see FIG. 2), and a mixer 42f (see FIG. 2). The 90 degrees phase shifter 42d generates a signal whose phase is shifted by 90° with respect to the modulation signal, and supplies the in-phase modulation signal and the 90 degrees phase-shifted modulation signal to the mixer 42e and the mixer 42f, respectively.

The amplified fluorescent signal is mixed, by the mixer 42e, with the in-phase modulation signal supplied as a reference signal, and is then supplied to the low-pass filter 42c. The amplified fluorescent signal is mixed, by the mixer 42f, with the 90 degrees phase-shifted modulation signal supplied as a reference signal, and is then supplied to the low-pass filter 42c.

The low-pass filter 42c performs filtering to extract, as a low-frequency signal, a signal of a predetermined frequency band lower than the frequency of the modulation signal from the fluorescent signal mixed with the modulation signal. Thereby, the frequency conversion unit 42 can determine a Re component (a component in-phase with the modulation signal) and an Im component (a component whose phase is shifted by 90 degrees with respect to the modulation signal) of the fluorescent signal which mainly include a signal component of a zero-frequency band. The thus determined Re component and Im component are supplied to the AD conversion unit 44.

The AD conversion unit 44 converts the supplied Re component and Im component into digital data. The AD conversion unit 44 includes an amplifier 44a and an AD converter 44b. The amplifier 44a amplifies the Re component and the Im component with a predetermined gain, and then supplies the amplified Re component and Im component to the AD converter 44b. The AD converter 44b converts the amplified Re component and Im component into digital data, and supplies the digitized Re component data and Im component data to the data processing unit 30.

The data processing unit 30 determines the phase delay θ of fluorescence and a fluorescence intensity signal by using the supplied Re component data and Im component data. Further, the data processing unit 30 calculates a fluorescence relaxation time τ by using the phase delay θ at the time when the value of the phase delay θ falls within a preset range and the value of the fluorescence intensity signal also falls within a preset intensity range, and calculates the fluorescence intensity of fluorescence at that time.

More specifically, the modulation signal is controlled by generating a control signal for adjusting the frequency of the modulation signal generated by the frequency variable oscillator 40a until the value of the calculated phase delay θ corresponds with a preset target value of, for example, 45 degrees within an acceptable range. Here, the acceptable range depends on a target calculation accuracy of a fluorescence relaxation time, and is, for example, ±5 degrees, ±2 degrees, or ±1 degree. When the value of the phase delay θ falls within the acceptable range previously set with respect to the target value, the control is settled.

Further, the data processing unit 30 generates a control signal for performing adjustment of the level of the DC component generated by the DC signal generator 40e or the gain of the variable amplifier 42a (adjustment of an operation amount) until the value of the calculated fluorescence intensity signal falls within the preset intensity range. Thereby, the data processing unit 30 can adjust the signal levels of the Re and Im components AD converted by the AD converter 44b.

Figure 4:
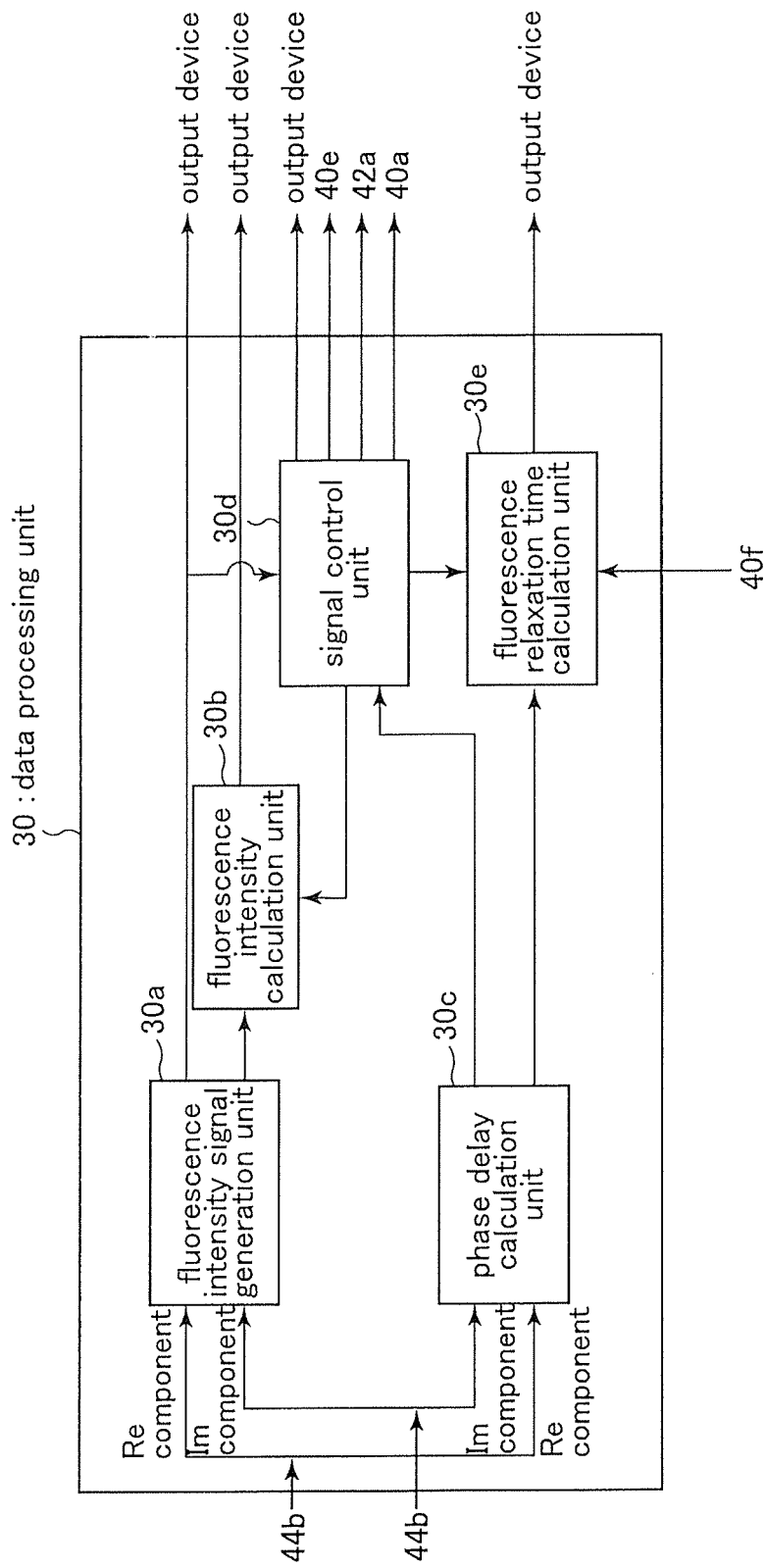
FIG. 4 is a schematic diagram illustrating the structure of a data processing unit of the flow cytometer illustrated in FIG. 1.

FIG. 4 is a schematic diagram illustrating the structure of the data processing unit 30. The data processing unit 30 includes a fluorescence intensity signal generation unit 30a, a fluorescence intensity calculation unit 30b, a phase delay calculation unit 30c, a signal control unit 30d, and a fluorescence relaxation time calculation unit 30e. These units are modules provided by executing a computer-executable program. That is, the data processing unit 30 performs its function by executing software on the computer.

The phase delay calculation unit 30c and the fluorescence relaxation time calculation unit 30e correspond to a processing unit that calculates, from the fluorescent signal, the phase delay of fluorescence with respect to the modulation signal, and further calculates the fluorescence relaxation time of fluorescence emitted by the sample 12 by using the calculated phase delay.

The fluorescence intensity signal generation unit 30a determines the square root of the addition of squares of the Re component data and the Im component data supplied from the AD converter 44b to generate a fluorescence intensity signal. The calculated fluorescence intensity signal is sent to the fluorescence intensity calculation unit 30b. The value of the fluorescence intensity signal is obtained as a result of adjusting the DC component of laser light and the gain of the variable amplifier 42a, and therefore widely varies depending on the result of adjusting them. Therefore, the fluorescence intensity calculation unit 30b corrects the fluorescence intensity signal by using information about the level of the DC component of intensity of laser light and the gain to calculate a fluorescence intensity. However, the correction of the fluorescence intensity signal to calculate a fluorescence intensity is not performed until the fluorescence intensity calculation unit 30b receives a decision instruction (which will be described later) given by the signal control unit 30d.

It is to be noted that the fluorescence intensity signal is time-series data calculated using the Re component data and the Im component data supplied continuously during the time period when the sample 12 passes through the measurement field irradiated with laser light.

In response to the decision instruction given by the signal control unit 30d, the fluorescence intensity calculation unit 30b corrects the fluorescence intensity signal calculated by the fluorescence intensity signal generation unit 30a by using information about the level of the DC component of intensity of laser light and the gain to calculate a fluorescence intensity. More specifically, the fluorescence intensity can be determined by dividing the value of the fluorescence intensity signal by a coefficient determined from the values of the control signals for adjusting the level of the DC component and the gain of the variable amplifier 42a. It is to be noted that the coefficient used for division is acquired by referring to LUT that associates the values of the control signals for adjusting the level of the DC component and the gain with the coefficients.

The DC component of laser light used for correction may be a signal value given by the control signal or the intensity of forward-scattered light measured by the light-receiving unit 24. The gain of the variable amplifier 42a may be a signal value given by the control signal or a value obtained by separately measuring the gain.

The decision instruction is given by the signal control unit 30d when the value of the fluorescence intensity signal during control generated by the fluorescence intensity signal generation unit 30a exceeds a predetermined setting value and reaches its maximum. Here, the predetermined setting value is a lower limit defining the preset range. The fluorescence intensity is determined by dividing the value of the fluorescence intensity signal at this time by the value of the control signal.

The adjustment of the level of the DC component generated by the DC signal generator 40e and the gain of the variable amplifier 42a (adjustment of operation amounts) is performed so that the value of the fluorescence intensity signal falls within the preset intensity range, but the fluorescence intensity becomes weak in the latter half of the time period when the sample 12 passes through the measurement field. At this time, the value of the fluorescence intensity signal does not reach its target value by the adjustment of the level of the DC component generated by the DC signal generator 40e and the gain of the variable amplifier 42a (adjustment of operation amounts), even when the operation amounts are maximized. On the other hand, in the stage from the first half to the middle of the time period when the sample 12 passes through the measurement field, the fluorescence intensity becomes gradually strong. Therefore, once the value of the fluorescence intensity signal falls within the preset range in this stage, the operation amounts are not adjusted and become constant. At this time, the value of the fluorescence intensity signal exceeds the setting value defining the preset range and reaches its maximum. Therefore, the fluorescence intensity is determined by dividing the value of the fluorescence intensity signal at this time by a coefficient determined from the values of the control signals at this time.

As described above, the value of a fluorescence intensity can be calculated by the above method, but may be calculated by integrating values obtained by dividing the value of the fluorescence intensity signal during control by a coefficient determined from the values of the control signals during the time period of control and then by dividing the integrated value by the control time.

The phase delay calculation unit 30c calculates the phase delay θ by calculating $\tan^{-1}(\text{Im}/\text{Re})$ (Im is the value of the Im component data and Re is the value of the Re component data) by using the supplied Re component data and Im component data. The calculated phase delay θ is supplied to the signal control unit 30d and the fluorescence relaxation time calculation unit 30e.

The fluorescence relaxation time calculation unit 30e determines, in response to the decision instruction from the signal control unit 30d, the fluorescence relaxation time τ according to the formula, $\tau = 1/(2\pi f) \cdot \tan \theta$ by using the phase delay θ supplied from the phase delay calculation unit 30c. The reason why the fluorescence relaxation time τ can be determined according to the above formula is that fluorescence is substantially a relaxation response of a first-order lag. It is to be noted that the frequency f of the modulation signal is the result of counting the frequency of the modulation signal supplied from the frequency counter 40f. Instead of the result of counting the frequency, the frequency f of the modulation signal may be a target frequency of the modulation signal determined by the control signal supplied from the signal control unit 30.

The signal control unit 30d determines whether the value of the fluorescence intensity signal supplied from the fluorescence intensity signal generation unit 30a and the phase delay θ supplied from the phase delay calculation unit 30c fall within their respective preset ranges, and generates a control signal according to the determination result.

More specifically, the signal control unit 30d controls the level of the DC component of laser light emitted from the light source unit 22 and the gain of the variable amplifier 44b so that the value of the fluorescence intensity signal falls within the preset range.

When determining that the value of the fluorescence intensity signal does not fall within the preset range, the signal control unit 30d generates a control signal for adjusting the signal level of the DC component generated by the DC signal generator 40e and supplies the control signal to the DC signal generator 40e. Thereby, the modulation signal whose signal level of the DC component has been adjusted is supplied to the laser driver 22c so that the intensity modulation of laser light is adjusted. Thereby, the modulation signal whose signal level of the DC component has been adjusted is supplied to the laser driver 22c. Further, the signal control unit 30d generates a control signal for adjusting the gain of the variable amplifier 42a provided just behind the light-receiving unit 26a to control the gain of the variable amplifier 42a. Here, the preset range used for determination is, for example, the range of values determined so that the quantization level of the maximum values of the time-series Re component data and Im component data quantized by AD conversion becomes 30% or higher of the total quantization level of AD conversion (in the case of 12 bits, the level is 308 or higher).

According to this embodiment, the modulation signal of the DC signal generator 40e and the gain of the variable amplifier 42 are both controlled, but either of them may be controlled.

Further, the signal control unit 30d always monitors the fluorescence intensity signal generated by the fluorescence intensity signal generation unit 30a and gives the decision instruction for correction when the value of the fluorescence intensity signal exceeds the predetermined setting value and reaches its maximum.

The signal control unit 30d also controls the frequency of the modulation signal so that the value of the phase delay θ comes close to 45 degrees. The phrase "comes close to a preset value" means that the value of the phase delay θ obtained after the control of the modulation signal is closer to a preset value than the value of the phase delay θ obtained before the control of the modulation signal. The value of the phase delay θ comes close to a preset target value by the control, but preferably converges within an acceptable range previously set with respect to the target value.

When the value of the phase delay θ does not correspond with a target value of 45 degrees within the acceptable range, the signal control unit 30d generates a control signal for adjusting the oscillation frequency of the frequency variable oscillator 40a and supplies the control signal to the frequency variable oscillator 40a. This makes it possible to supply the modulation signal whose frequency has been adjusted to the laser driver 22c so that the intensity modulation of laser light is adjusted.

When the value of the fluorescence intensity signal falls within the preset range and the value of the phase delay θ falls within the preset range, the signal control unit 30d determines that the phase delay θ has been obtained with high accuracy, and gives the decision instruction for calculation of a fluorescence intensity and a fluorescence relaxation time to the fluorescence intensity calculation unit 30b and the fluorescence relaxation time calculation unit 30e.

As described above, when the value of the fluorescence intensity signal and the value of the phase delay θ both fall within their respective preset ranges, the phase delay θ is obtained with high accuracy. Thereby, a fluorescence relaxation time can be calculated with high accuracy. According to the present invention, the phase delay θ is obtained with high accuracy by at least determining whether the value of the fluorescence intensity signal falls within the preset range.

Figure 5A:
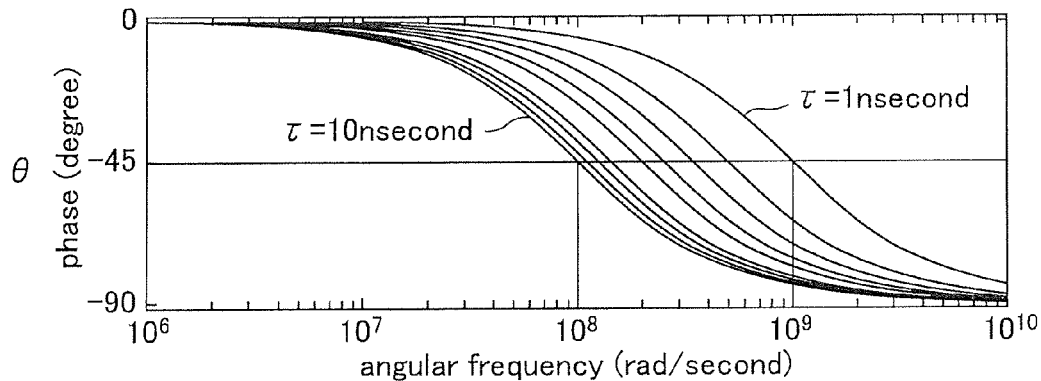
FIGS. 5A and 5B are graphs for explaining the effect of adjustment of a phase delay θ performed in the fluorescence detection device according to the present invention and a phase detection method according to the present invention.

FIG. 5A is a graph illustrating the relationship between the frequency (angular frequency $2\pi f$) at which the intensity of laser light is modulated and the phase delay θ of fluorescence emitted by irradiation with the laser light, which is determined for different values of the fluorescence relaxation time τ.

When the phase delay θ is 45 degrees, the angular change of the phase delay θ with respect to the angular frequency $2\pi f$ is maximized. That is, the sensitivity of the phase delay θ is high at an angle of 45 degrees. Therefore, by controlling the frequency of the modulation signal so that the phase delay θ comes close to 45 degrees, the sensitivity of the phase delay θ to be calculated can be made high. Thereby, the phase delay θ can be calculated with high accuracy.

Figure 5B:
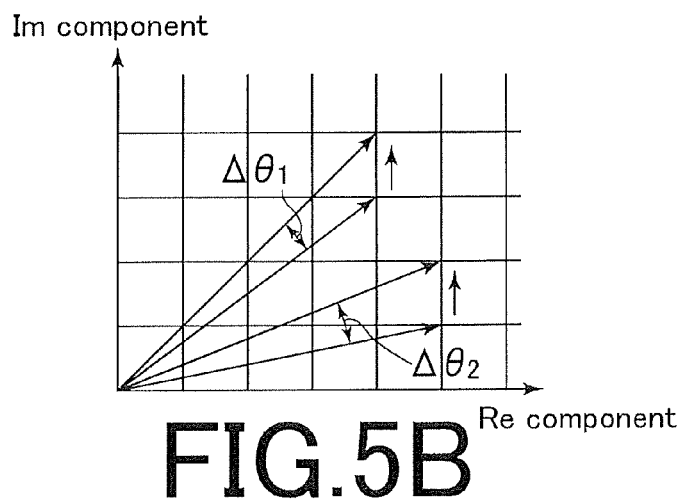

As illustrated in FIG. 5B, assuming that the quantization level of AD conversion is shifted by one due to the error of the Re or Im component caused by AD conversion performed by the AD converter 44b, the change $\Delta\theta_1$ of the phase delay at the time when the phase delay θ corresponds with 45 degrees within the acceptable range is smaller than the change $\Delta\theta_2$ of the phase delay at the time when the phase delay θ falls within a range other than the acceptable range. Therefore, the error of the phase delay θ caused by a quantization error can be reduced when the phase delay θ corresponds with 45 degrees within the acceptable range.

Figure 5C:
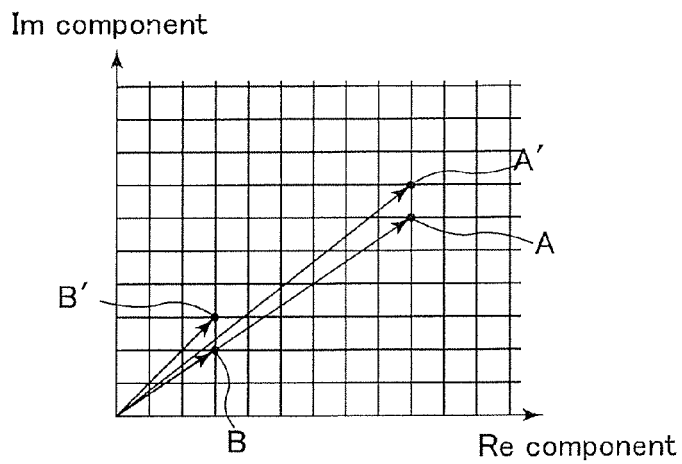
FIG. 5C is a graph for explaining the effect of adjustment of a fluorescence intensity.

Further, as illustrated in FIG. 5C, assuming that the quantization level of the point A is high and the quantization level of the point B is low, the change of the phase angle at the time when the point B is shifted to the point B' due to the error of the Im component is larger than that at the time when the point A is shifted to the point A' due to the error of the Im component. Therefore, by allowing the value of the fluorescence intensity signal calculated from the Re component data and the Im component data to fall within the preset range, the phase delay θ can be determined with a given accuracy even when an error is caused by AD conversion.

Figure 6:
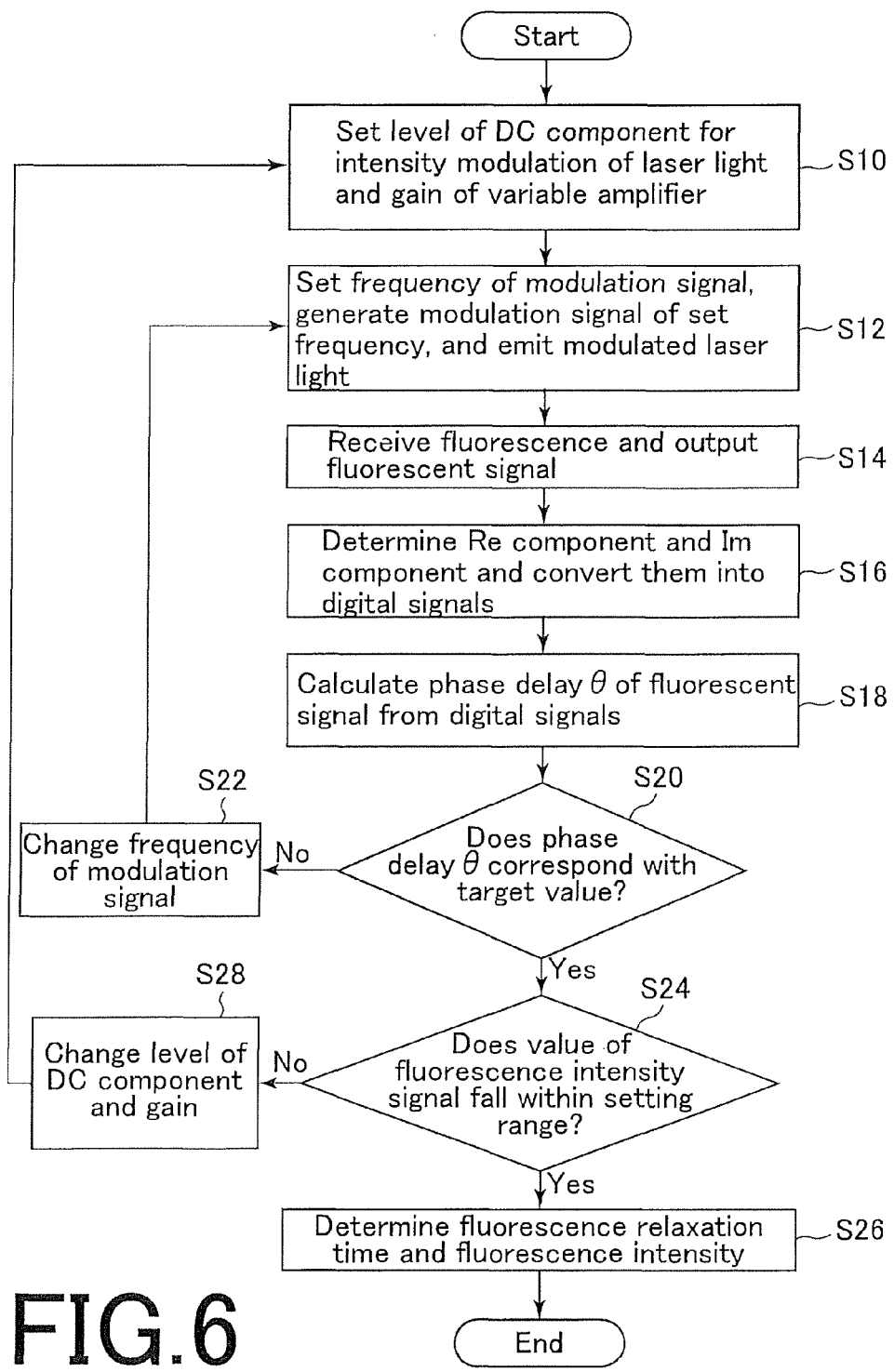
FIG. 6 is a flow chart for explaining one embodiment of the fluorescence detection method according to the present invention.

FIG. 6 is a flow chart for explaining one embodiment of a fluorescence detection method using the fluorescence detection device 10. According to the method of the embodiment, the DC component of the intensity of laser light, the amplification gain of a fluorescent signal just after receiving fluorescence, and the frequency of a modulation signal are adjusted to calculate a fluorescence intensity and a fluorescence relaxation time.

First, the signal level of the DC component of a modulation signal to modulate the intensity of laser light and the gain of the variable amplifier 42a of the frequency conversion unit 42 are set by the modulation signal control unit 40 based on control signals supplied from the data processing unit 30 (Step S10). At the beginning of processing, the signal level of the DC component and the gain are set to default values.

Then, the frequency of the modulation signal is set by the modulation signal control unit 40 based on a control signal supplied from the data processing unit 30. For example, the frequency is set to a default value. A modulation signal is generated using the thus set signal level of the DC component, gain, and frequency of the modulation signal, and intensity-modulated laser light is emitted from the laser light source 22a (Step S12).

Then, fluorescence emitted by the sample 12 passing through the measurement field by irradiation with laser light is received by the light-receiving unit 26a, and a fluorescent signal is outputted (Step S14).

Then, the fluorescent signal is amplified with the gain set by the variable amplifier 42a, supplied to the mixers 42e and 42f, and mixed with the modulation signal to determine a Re component and an Im component. Further, the Re component and the Im component are converted by the AD converter 44 into digital signals so that Re component data and Im component data are obtained (Step S16).

Then, the phase delay calculation unit 30c of the data processing unit 30 calculates the phase delay θ of the fluorescent signal from the digitized Re component data and Im component data (Step S18).

Then, the signal control unit 30d determines whether the calculated phase delay θ corresponds with a preset target value of 45 degrees within an acceptable range (Step S20). When the phase delay θ corresponds with a target value of 45 degrees within the acceptable range, a control signal for changing the frequency of the modulation signal is generated and supplied to the frequency variable oscillator 40a. As a result, the frequency of the modulation signal is changed (Step S22). Here, the changing of the frequency is performed using the calculated phase delay θ so that the frequency becomes a value calculated by, for example, frequency $f=2\pi f_1/\tan(\theta)$ ($f_1$ is the current frequency of the modulation signal).

A series of Steps S10 to S22 is repeated until the phase delay θ corresponds with a target value of 45 degrees within the acceptable range.

When the result of the determination in Step S20 is YES, the signal control unit 30 further determines whether the value of a fluorescence intensity signal falls within a preset range (Step S24). When the value of the fluorescence intensity signal falls within the preset range (i.e., when the result of the determination is YES), the signal control unit 30 gives a decision instruction for calculation of a fluorescence intensity and a fluorescence relaxation time to the fluorescence intensity calculation unit 30b and the fluorescence relaxation time calculation unit 30e. In this way, the fluorescence intensity calculated by the fluorescence intensity calculation unit 30b and the fluorescence relaxation time calculated by the fluorescence relaxation time calculation unit 30e are determined as measurement results of the sample 12 (Step S26).

When the value of the fluorescence intensity signal does not fall within the preset range (i.e., when the result of the determination is No), the signal level of the DC component used for the modulation signal and the gain are changed (Step S28), and the processing is returned to Step S10.

In this way, a series of Steps S10 to S24 and S28 is repeated until the value of the fluorescence intensity signal falls within the preset range. At the time when the value of the fluorescence intensity signal falls within the preset range and reach its maximum, the value of the fluorescence intensity signal is corrected based on the values of the control signals for adjusting the signal level of the DC component and the gain and is then outputted.

The calculated measurement results are outputted together with the signal level of the DC component, the gain, and the frequency of the modulation signal to an output device (not illustrated) such as a display or a printer.

As described above, the fluorescence detection method uses a process in which the determination as to whether the phase delay θ falls within a setting range is made, and when the determination result is YES, the determination as to whether the value of the fluorescence intensity signal falls within a setting range is made. However, the method according to this embodiment may use a process in which the determination as to whether the value of the fluorescence intensity signal falls within a setting range is made, and when the determination result is YES, the determination as to whether the phase delay θ falls within a setting range is made.

Such a control using the flow cytometer illustrated in FIG. 1 may be performed in the following manner. Assuming that the sample 12 comprises a plurality of sample particles and the sample particles intermittently pass through the measurement field irradiated with laser light one by one at a constant rate, the signal control unit 30d begins the control of the signal level of the DC component of the modulation signal and the gain of the variable amplifier 42a just after the sample particle begins to pass through the measurement field irradiated with laser light so that the value of the fluorescence intensity signal falls within a preset value. Then, the data processing unit 30 finds operation amounts allowing the value of the fluorescence intensity signal to fall within the preset range before the sample particle passes over the measurement field irradiated with laser light. The data processing unit 30 calculates a fluorescence relaxation time from a phase delay obtained under the condition of the found operation amounts and the frequency of the modulation signal. Further, the data processing unit 30 calculates a fluorescence intensity from the value of the fluorescence intensity signal and the operation amounts when the value of the fluorescence intensity signal and the operation amounts is set. At the same time, the frequency of the modulation signal is also controlled.

When a measurement device, in which the sample 12, contained in a certain container such as a cuvette and remaining at rest, is irradiated with laser light, is used, the following measurement method may be employed. Assuming that the sample 12, contained in a certain container and remaining at rest, is irradiated with laser light, the data processing unit 30 controls the signal level of the DC component of the modulation signal and the gain of the variable amplifier 42a so that the value of the fluorescence intensity signal falls within a preset range, and calculates a fluorescence relaxation time from the phase delay of fluorescence emitted by a measurement object at the time when the control is settled. The data processing unit 30 also calculates a fluorescence intensity from the value of the fluorescence intensity signal and operation amounts at the time when the control is settled. At the same time, the frequency of the modulation signal is also controlled.

As described above, the phase delay θ and the fluorescence intensity can be determined with a given accuracy over wide ranges by adjusting the signal levels of the Re component and the Im component by using the fluorescence intensity signal obtained from the fluorescent signal. When the signal levels of the Re component and the Im component are low, the Re component and the Im component may contain an error due to contamination by noise generated by the IQ mixer 42b, the low-pass filter 42c, the AD converter 44b, and the like. If AD conversion is performed in this state, a quantization error is increased so that the error of the phase delay θ calculated using the AD converted Re and Im components is increased. However, according to this embodiment, the signal levels of the Re and Im components can be maintained constant by allowing the fluorescence intensity signal calculated from the Re and Im components to fall within a preset range, thereby reducing the error of the phase delay θ to a certain level or suppressing the error of the phase delay θ.

According to the embodiment, it is possible to make the contribution of a phase delay to a fluorescence relaxation time not nonlinear but constant to calculate a fluorescence relaxation time by adjusting the frequency of the modulation signal for modulating the intensity of laser light so that a phase delay comes close to a target value of 45 degrees. Therefore, according to the embodiment, it is possible to expand the range of a fluorescence relaxation time that can be calculated with a given accuracy. For example, assuming that fluorescence is a relaxation response of a first-order lag, the embodiment allows tan θ (θ is defined as a phase delay), which is a nonlinear part, to have a substantially constant value irrespective of a fluorescence relaxation time. This makes it possible to prevent the calculation accuracy of a fluorescence relaxation time from varying due to a great difference in the contribution of tan θ between a case of large phase delay θ and a case of small phase delay θ.

Particularly, by allowing the phase delay θ to come close to 45 degrees, the sensitivity of the phase delay to be calculated to the frequency of the modulation signal can be made high. This makes it possible to calculate a fluorescence relaxation time with high accuracy.

In the above description, the phase delay and the fluorescence intensity signal are both controlled, but only the fluorescence intensity signal may be controlled to determine whether the value of the fluorescence intensity signal falls within a preset range without performing the control of the phase delay to determine whether the phase delay θ corresponds with a target value within an acceptable range.

As described above, according to the embodiment, a fluorescence intensity and a fluorescence relaxation time are calculated by adjusting the operation amount of at least one of the signal level of the DC component of the modulation signal used for intensity modulation and the gain of the amplifier so that the value of the fluorescence intensity signal calculated using a digitized in-phase component and a digitized 90 degrees phase-shifted component falls within a preset range. This makes it possible to reduce the errors of a fluorescence intensity and a phase delay caused by a quantization error during AD conversion to a certain level or less. Therefore, according to the present invention, it is possible to expand the range of a fluorescence intensity that can be calculated with a given accuracy and the range of a fluorescence relaxation time that can be calculated with a given accuracy.

Further, according to the embodiment, the frequency for intensity modulation is controlled so that the phase delay of fluorescence comes close to 45 degrees while the operation amount of at least one of the signal level of the DC component of the modulation signal used for intensity modulation and the gain of the amplifier is controlled so that the value of the light intensity falls within a preset range. This makes it possible to calculate a fluorescence intensity and a fluorescence relaxation time with high accuracy over wide ranges. The fluorescence relaxation time can be calculated with high accuracy even when a difference in the length of the fluorescence relaxation time is large.

The fluorescence detection device and fluorescence detection method according to the present invention have been described above in detail, but the present invention is not limited to the above embodiments and it should be understood that various changes and modifications may be made without departing from the scope of the present invention.

DESCRIPTION OF REFERENCE NUMERALS 10 flow cytometer
12 sample
22 laser light source unit
22a laser light source
22b, 24b, 26b lens systems
22c laser driver
24, 26 light-receiving units
24a, 26a photoelectric converters
26c shielding plate
28 control/signal processing unit
30 data processing unit (computer)
30a fluorescence intensity signal generation unit
30b fluorescence intensity calculation unit
30c phase delay calculation unit
30d signal control unit
30e fluorescence relaxation time calculation unit
32 tube
34 collection vessel
40 modulation signal control unit
40a frequency variable oscillator
40b power splitter
40c, 40d, 44a amplifiers
40e DC signal generator
42 frequency conversion unit
42a variable amplifier
42b IQ mixer
42c low-pass filter
42d 90° phase shifter
42e, 42f mixers
44 A/D conversion unit
44b A/D converter

The invention claimed is:
1. A fluorescence detection device by processing a fluorescent signal obtained by receiving fluorescence emitted by a measurement object which is irradiated with laser light, the device comprising:
a light source unit operable to emit laser light with which a measurement object is irradiated while modulating an intensity of the laser light;
a light-receiving unit operable to output a fluorescent signal of fluorescence emitted by the measurement object irradiated with the laser light;

a light source control unit operable to generate a modulating signal for modulating the intensity of the laser light emitted from the light source unit;

a first processing unit that includes an amplifier that amplifies the fluorescent signal outputted by the light-receiving unit, a mixer that generates a component of the amplified fluorescent signal in phase with the modulation signal and a 90 degrees phase-shifted component of the amplified fluorescent signal which is phase-shifted by 90 degrees with respect to the modulation signal, and an AD converter that digitizes the generated in-phase component and 90 degrees phase-shifted component;

a second processing unit operable to calculate, by using the digitized in-phase component and the 90 degrees phase-shifted component, a fluorescence intensity signal and a phase delay of the fluorescence with respect to the modulation signal and operable to calculate, by using the calculated fluorescence intensity signal and the phase delay, a fluorescence intensity and a fluorescence relaxation time of the fluorescence emitted by the measurement object; and a signal control unit operable to control an operation amount of at least one of a signal level of a DC component of the modulation signal used for intensity modulation and a gain of the amplifier so that a value of the fluorescence intensity signal falls within a preset range.

2. The fluorescence detection device according to claim 1, wherein
after the signal control unit finds the operation amount at a time when the value of the fluorescence intensity signal falls within the preset range, the second processing unit calculates, by using the found operation amount and the value of the fluorescence intensity signal obtained under a condition of the found operation amount, the fluorescence intensity of the fluorescence emitted by the measurement object and calculates, by using the phase delay, the fluorescence relaxation time of the fluorescence emitted by the measurement object.

3. The fluorescence detection device according to claim 2, wherein
the measurement object includes a plurality of sample particles which intermittently pass through a measurement field irradiated with the laser light one by one at a constant rate, and
wherein the signal control unit begins to control the operation amount just after each of the sample particles begins to pass through the measurement field irradiated with the laser light so that the value of the fluorescence intensity signal falls within the preset range, and finds the operation amount allowing the value of the fluorescence intensity signal to fall within the preset range before each of the sample particles passes over the measurement field irradiated with the laser light, and calculates the fluorescence relaxation time from the phase delay obtained under a condition of the found operation amount and a frequency of the modulation signal, and calculates the fluorescence intensity by using the value of the fluorescence intensity signal falling within the preset range and the operation amount.

4. The fluorescence detection device according to claim 2, wherein
the measurement object, contained in a certain container and remaining at rest, is irradiated with the laser light, and wherein the signal control unit controls the operation amount so that a value of the fluorescence intensity falls within a preset range, and wherein the second processing unit calculates the fluorescence intensity and the fluorescence relaxation time when the control of the operation amount is settled.

5. The fluorescence detection device according to claim 1, wherein
the signal control unit controls not only the operation amount but also a frequency for the intensity modulation so that an angle of the phase delay of the fluorescence comes close to 45 degrees and calculates the fluorescence intensity and the fluorescence relaxation time by using the value of the fluorescence intensity signal and the phase delay at a time when the control of the frequency is settled.

6. A fluorescence detection method by processing a fluorescent signal obtained by receiving fluorescence emitted by a measurement object which is irradiated with laser light, the method comprising the steps of:

generating a modulation signal by setting a frequency for modulating an intensity of laser light emitted from a laser light source unit and a signal level of a DC component to modulate laser light by using the modulation signal;

obtaining a fluorescent signal of fluorescence emitted by a measurement object irradiated with the laser light;

amplifying the fluorescent signal, generating a in phase-component of the amplified fluorescent signal with the modulation signal and a 90 degrees phase-shifted component of the amplified fluorescent signal which is phase-shifted by 90 degrees with respect to the modulation signal, and digitizing the generated in-phase component and the 90 degrees phase-shifted component;

calculating, by using the digitized in-phase component and the 90 degrees phase-shifted component, a fluorescence intensity and a phase delay of the fluorescence with respect to the modulation signal;

controlling an operation amount of at least one of the signal level of the DC component and a gain of the amplification so that the fluorescence intensity falls within a preset range; and calculating, by using the in-phase component and the 90 degrees phase-shifted component obtained under a condition of the operation amount at a time when a value of the fluorescence intensity falls within the preset range, a value of the fluorescence intensity signal and the phase delay and calculating, by using the calculated value of the fluorescence intensity signal and the calculated phase delay, a fluorescence intensity and a fluorescence relaxation time of the fluorescence emitted by the measurement object.

7. The fluorescence detection method according to claim 6, wherein
after the operation amount at a time when a value of the fluorescence intensity signal falls within a preset range is found, the fluorescence intensity and fluorescence relaxation time of the fluorescence emitted by the measurement object are calculated by using the value of the fluorescence intensity signal and the phase delay obtained under a condition of the found operation amount.

8. The fluorescence detection method according to claim 7, wherein
the measurement object includes a plurality of sample particles which intermittently pass through a measurement field irradiated with the laser light one by one at a constant rate, and
wherein the operation amount begin to be controlled just after each of the sample particle begins to pass through the measurement field irradiated with the laser light so that the value of the fluorescence intensity falls within the preset range, and the operation amount allowing the value of the fluorescence intensity signal to fall within the preset range is found before each of the sample particles passes over the measurement field irradiated with the laser light, and the fluorescence relaxation time is calculated from the phase delay obtained under a condition of the found operation amount and the frequency of the modulation signal, and the fluorescence intensity is calculated by using the value of the fluorescence intensity signal falling within the preset range and the operation amount.

9. The fluorescence detection method according to claim 7, wherein
the measurement object, contained in a certain container and remaining at rest, is irradiated with the laser light, and
wherein the operation amount is controlled so that the value of the fluorescence intensity falls within the preset range, and the fluorescence intensity and the fluorescence relaxation time are calculated by using the value of the fluorescence intensity signal and the phase delay of the fluorescence emitted by the measurement object at a time when the control of the operation amount is settled.

10. The fluorescence detection method according to claim 6, wherein
in the step of controlling the operation amount, the operation amount as well as a frequency for the intensity modulation is controlled so that an angle of the phase delay of the fluorescence comes close to 45 degrees, and the fluorescence intensity and the fluorescence relaxation time are calculated using the value of the fluorescence intensity signal and the phase delay at a time when the control of the frequency is settled.

* * * * *